United States Patent [19]
McAndrew et al.

[11] Patent Number: 5,261,452
[45] Date of Patent: Nov. 16, 1993

[54] CRITICAL ORIFICE DILUTION SYSTEM AND METHOD

[75] Inventors: James J. F. McAndrew, Lockport; Michael D. Brandt, Chicago, both of Ill.

[73] Assignee: American Air Liquide, Walnut Creek, Calif.

[21] Appl. No.: 858,679

[22] Filed: Mar. 27, 1992

Related U.S. Application Data

[63] Continuation-in-part of Ser. No. 662,847, Mar. 1, 1991, abandoned.

[51] Int. Cl.$^5$ ............................................. B01F 3/02
[52] U.S. Cl. .................................... 137/606; 137/100; 137/896
[58] Field of Search ............... 137/98, 100, 606, 896, 137/897, 898, 7; 366/339

[56] References Cited

U.S. PATENT DOCUMENTS

| | | | |
|---|---|---|---|
| 3,087,004 | 4/1963 | Thorsheim | 137/98 X |
| 3,464,434 | 9/1969 | Nielsen | 137/98 |
| 3,521,658 | 7/1970 | Sandow. | |
| 3,841,344 | 10/1974 | Slack | 137/606 X |
| 3,905,394 | 9/1975 | Jerde | 137/599 |
| 4,408,893 | 10/1983 | Rice | 366/339 |
| 4,498,496 | 2/1985 | Barcellona | 137/606 X |
| 4,842,827 | 6/1989 | Graf et al. . | |
| 4,878,510 | 11/1989 | Kasper et al. . | |

FOREIGN PATENT DOCUMENTS

| | | |
|---|---|---|
| 2123961 | 12/1971 | Fed. Rep. of Germany . |
| 1334109 | 8/1987 | U.S.S.R. . |
| 1209603 | 10/1970 | United Kingdom ............... 366/339 |
| 1411078 | 10/1975 | United Kingdom . |
| 2163216 | 2/1986 | United Kingdom . |

OTHER PUBLICATIONS

Soviet Inventions Illustrated Week B48, Jan. 16, 1980, Derwent Publications Ltd., London, AN L1921B/48 & SU-A-652 445 (Agranovskii) Mar. 18, 1979, Abstract.
Soviet Inventions Illustrated Section Ch, Week 8848, Jan. 18, 1989, Derwent Publications Ltd., London Class J, AN 88-344607/48 & SU-A-1 392 381 (Karashev) Apr. 30, 1988, Abstract.
Measurement Techniques, vol. 24, No. 3, Mar. 1981, New York, Roman'ko et al., "Metrological Certification of a dynamic Gas-mixing Installation", p. 244.

Primary Examiner—Robert G. Nilson
Attorney, Agent, or Firm—Curtis, Morris & Safford

[57] ABSTRACT

An apparatus and method are provided for preparing low concentration gas phase calibration standards. The flows of a standard mixture of impurity in a gas and a dilution gas are controlled by regulating the pressure upstream of respective calibrated orifices. The pressures of the gas flows are regulated such that a critical flow condition is maintained through the orifices. The two flows are then combined to obtain a known dilution of the impurity in the gas.

19 Claims, 5 Drawing Sheets

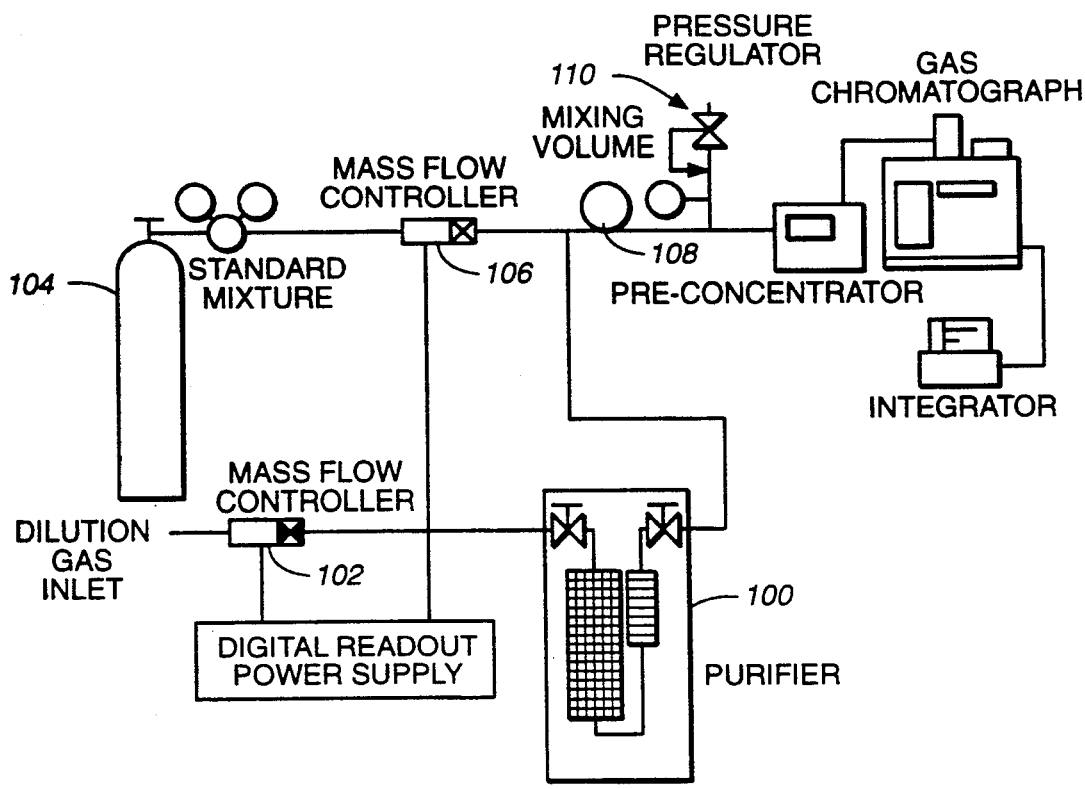
DILUTION SETUP USING MASS FLOW CONTROLLERS
FIG._1
*PRIOR ART*
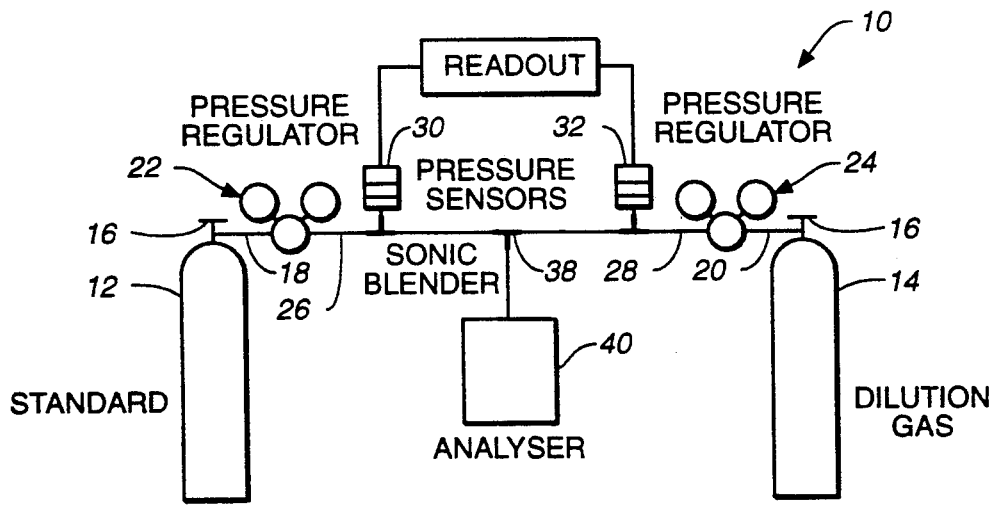
DILUTION SETUP USING "SONIC BLENDER"
FIG._2

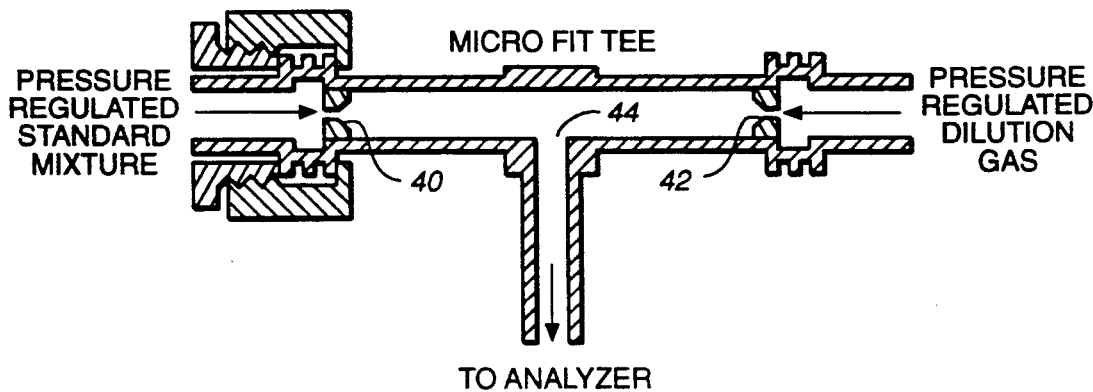
FIG._3
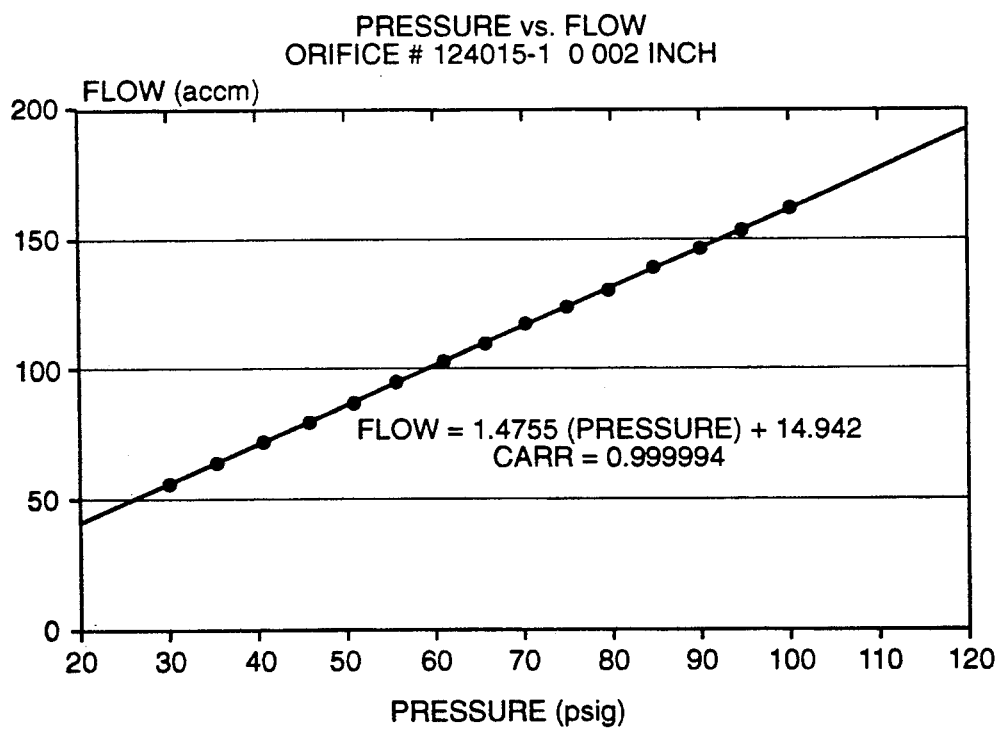
FIG._4

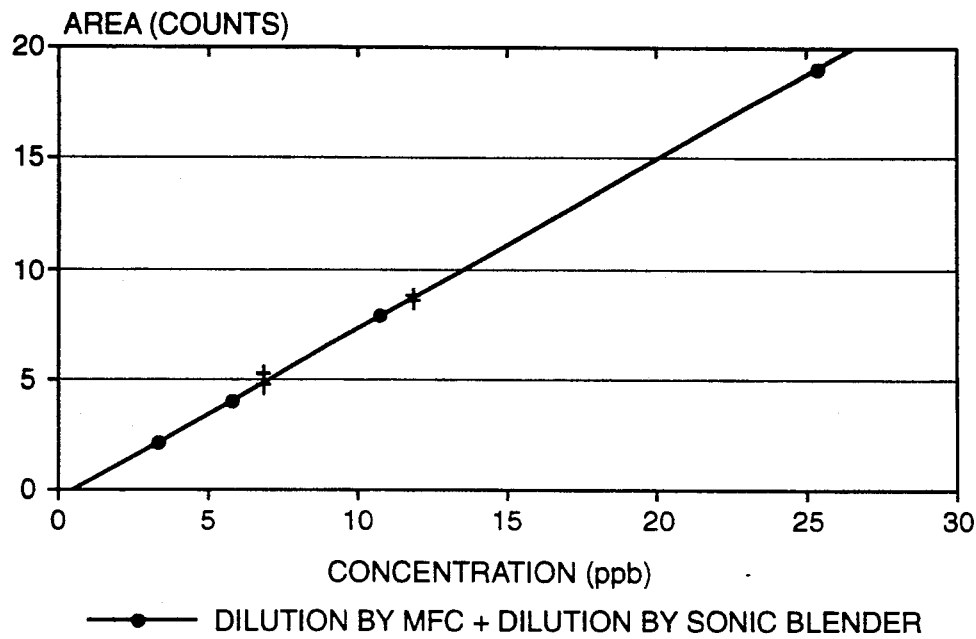
FIG._5
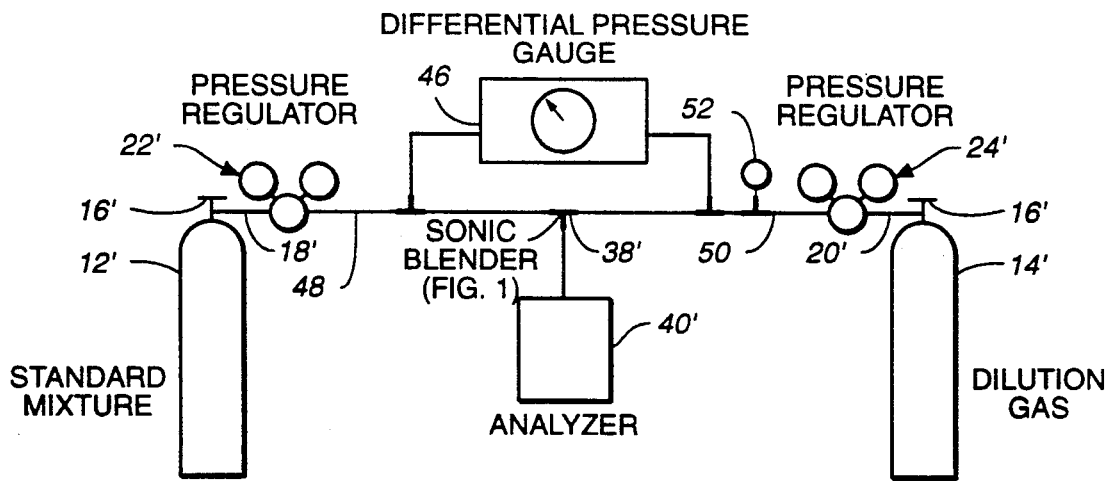
FIG._6

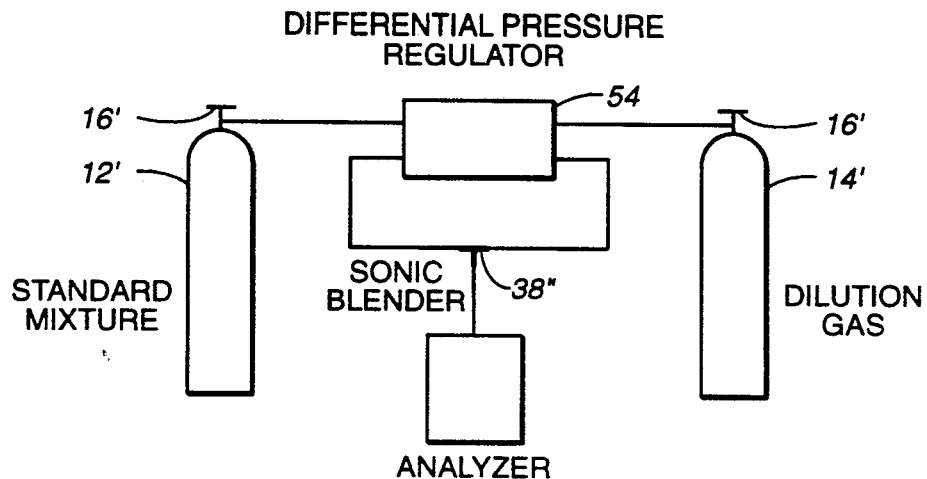
FIG._7
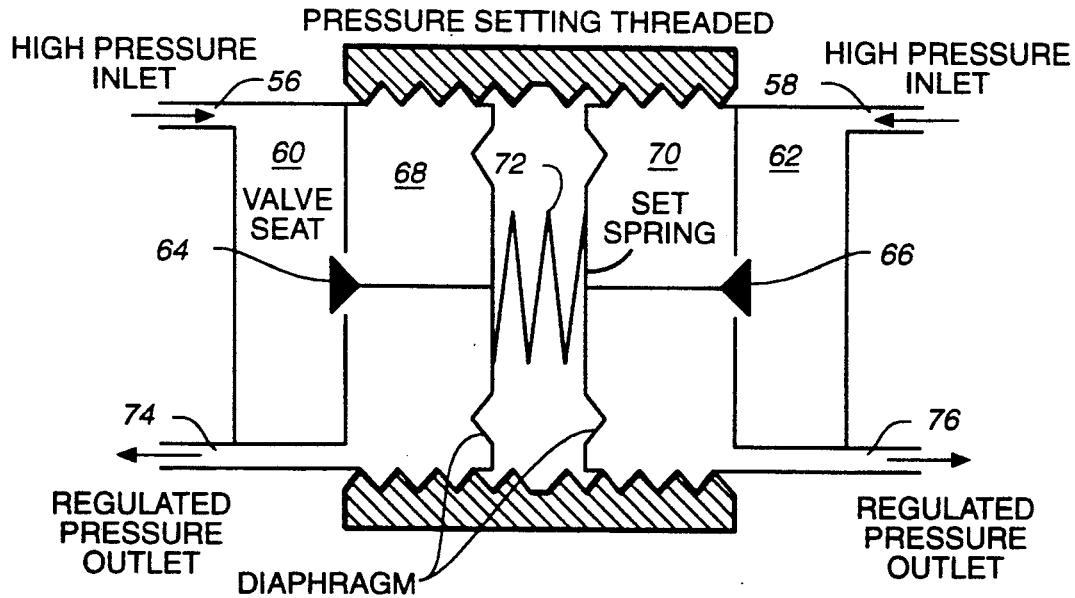
FIG._8

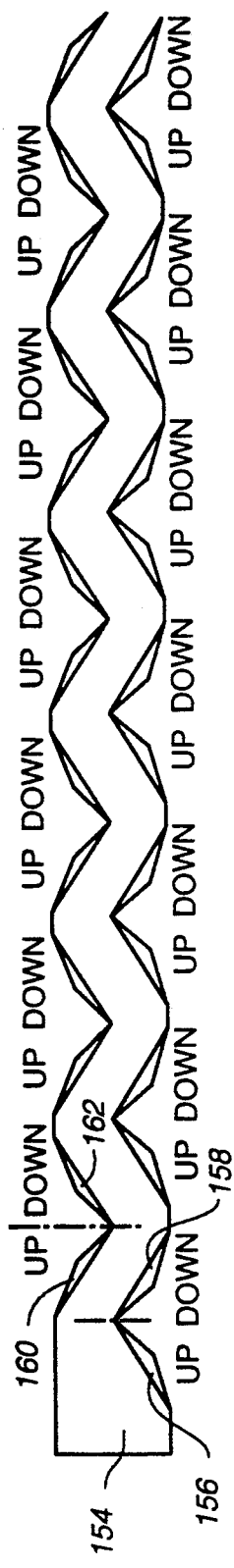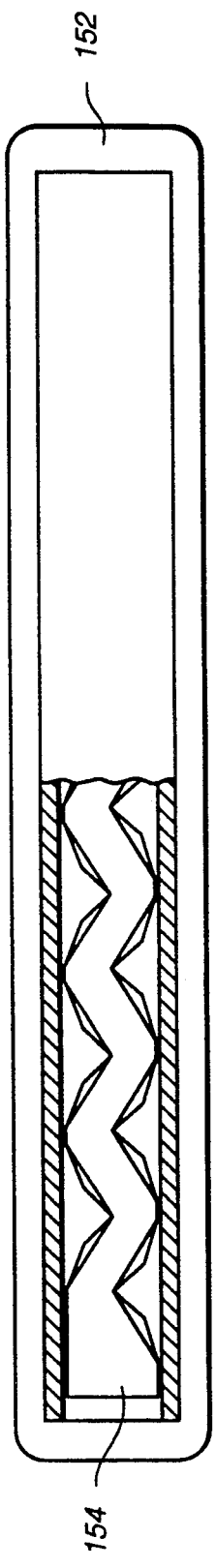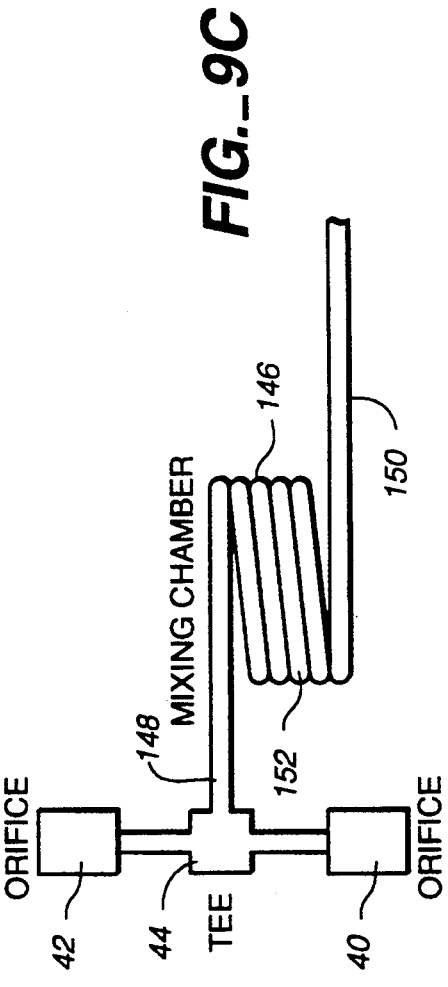

CRITICAL ORIFICE DILUTION SYSTEM AND METHOD

This is a continuation-in-part of application Ser. No. 07/662,847 filed Mar. 1, 1991, now abandoned.

BACKGROUND OF THE INVENTION

1. Field of the Invention

The present invention relates generally to gas phase calibration standards for the calibration of analytical instruments and more particularly to field preparation of low concentration gas phase calibration standards.

2. Description of Related Art

Laboratory or commercial preparation of low concentration standards is known in the art. For example, a dilution system using mass flow controllers to effect a precise proportion of two gases is shown in FIG. 1. This system comprises a source of pure gas, comprised of a container of gas (not shown) and a purifier 100, whose flow is controlled by a first thermal mass flow control device ("MFC") 102. It further comprises a source of a "standard mixture" 104 (a mixture of pure gas with a known quantity of some impurity) whose flow is controlled by a second MFC 106. The two flows from the MFCs 102 and 106 are combined in a mixing volume 108 such that the ratio of the flows, as regulated by the MFCs 102 and 106, determines the dilution ratio. An excess flow venting device 110 (e.g. a pressure regulator as shown in FIG. 1) provides a means of controlling the flow of the mixed gases to the ultimate destination. This system requires electric power to operate and needs time to reach thermal equilibrium. It is bulky and expensive and not conducive to work in the field. Other commercial systems which operate by combining flows through complicated arrays of capillaries are difficult to manufacture and also very expensive.

In practice, low concentration standards are frequently prepared well in advance of their use and stored in gas cylinders. This pre-mixing to produce a diluted gas of fixed concentration can become a problem when the desired low concentration impurities (typically organic compounds) are suspected of interacting destructively with the internal surfaces of the storage vessel.

For many applications where gas phase calibration standards (consisting of an accurately known concentration of one or more impurities in a balance of pure gas) are required, it is desirable to dilute a standard at high concentration with a pure gas to obtain the desired concentration. Such an approach would avoid many of the problems associated with the storage of pre-mixed standards and provide multiple concentration levels.

Flow of gases through an orifice under "critical" conditions is a relatively well understood phenomenon described in standard texts on fluid dynamics. Several of its features have been employed in a number of different applications.

For example, U.S. Pat. No. 4,878,510 to Kasper et al. discloses a method which avoids the formation of droplets by condensation of vapors during the expansion of a highly compressed gas through a critical orifice. Co-pending application Ser. No. 107,177 to Wen et al. assigned to the assignee of the present invention discloses a method for quantifying the concentration of condensible vapors in a carrier gas by using the minimum pressure drop across a critical orifice to cause droplet formation and then detecting the number of droplets for comparison with the volume of gas which has passed through the critical orifice.

Several applications have employed critical orifices as flow control devices. Soviet Union Patent No. 1,334,109 to Isakov et al. relates to a method to control liquid flow by first vaporizing a liquid, passing the vapor through a critical orifice and then recondensing the liquid. U.S. Pat. No. 4,842,827 to Graf et al. describes the use of critical orifices to control the flow of gases to a vacuum system. A high purity "fixed" gas is used to measure the orifice size which is then used to calculate the flow of reactive or toxic gases through the orifice.

Co-pending application Ser. No. 437,615 now U.S. Pat. No. 5,054,309 and Ser. No. 437,623 now U.S. Pat. No. 5,157,957 to Mettes et al. assigned to the assignee of the present invention disclose a process and apparatus to generate low concentration calibration mixtures for testing and/or calibrating analytical instruments such as an atmospheric pressure ionization mass spectrometer. The Mettes inventions employ critical orifices to simultaneously control the flow of multiple gas streams to achieve a known dilution. However, these inventions relate to a system which is large and complicated and is designed for laboratory use. Still further, the system requires multiple mixing steps with more than two gas sources and a moisture generator.

OBJECTS OF THE INVENTION

Therefore, it is an object of the present invention to overcome the drawbacks of the prior art.

It is another object of the present invention to provide a portable apparatus capable of producing low concentration gas phase calibration standards.

It is a further object of the present invention to provide an apparatus and method to produce varying low concentrations of gas phase calibration standards.

SUMMARY OF THE INVENTION

The present invention employs two calibrated orifices to control the flow of two gases (a standard gas and a dilution gas) in proportions determined by the upstream pressure, the density of the gases and the size of the orifices. In one embodiment of the present invention, the system comprises two gas supplies of sufficient pressure which are regulated to predetermined pressures which will result in a predictable flow rate through each orifice. Typically, one of these gas supplies is a container of a particular concentration of gas (a standard gas) and the other is a container of dilution gas. The gases flow through respective pressure regulators, which are adjusted in response to downstream pressure sensors (gauges), out of their respective orifices, into a blending chamber where the desired dilution is achieved and then directed toward the instrument to be calibrated.

A second embodiment of the present invention replaces the two pressure sensors (gauges) with a single, standard differential pressure gauge. This eliminates inherent cumulative errors introduced by the two independent gauges.

A third embodiment of the present invention incorporates an equal pressure regulating device in place of the differential pressure gauge of the second embodiment of the present invention. In this embodiment, since the regulating device does not possess the capacity to vary the relative upstream pressures to the orifices, a single dilution is generated.

BRIEF DESCRIPTION OF THE DRAWINGS

In the drawings:

FIG. 1 is a schematic diagram of a dilution system employing a prior art mass flow controller;

FIG. 2 is a schematic diagram of a first embodiment of the present invention;

FIG. 3 is a cross-sectional view of the "sonic blender" of the present invention;

FIG. 4 is a graph of the pressure to flow relationship for a typical calibrated orifice used in accordance with the present invention;

FIG. 5 is a graph comparing dilution of a standard by a mass flow controller and by an embodiment of the present invention;

FIG. 6 is a schematic diagram of a second embodiment of the present invention;

FIG. 7 is a schematic diagram of a third embodiment of the present invention;

FIG. 8 is a cross-sectional view of the differential pressure regulator of the third embodiment of the present invention; and FIGS. 9a, b, c represent a further embodiment of the invention with an additional mixing chamber comprising a convoluted path.

DETAILED DESCRIPTION OF THE INVENTION

In accordance with the present invention, a low concentration gas mixture typically of organic compounds in nitrogen or air (on the order of parts per billion (by volume), is generated at the time of use by dilution of a parts per million level standard (by volume). The generation of the low concentration standard at the time of use is desirable because it is believed that mixtures at the parts per million level are more stable in gas cylinders than those at the much lower parts per billion level.

FIG. 2 depicts a first embodiment of the present invention. In this embodiment, the system 10 includes two cylinders of gas; a first cylinder 12 of a standard mixture and a second cylinder 14 of a dilution gas. Each cylinder has a standard valve 16 to release the gas from within. Conduits 18 and 20 carry the gas from the cylinders to respective pressure regulators 22 and 24. Preferably, the pressure regulators 22 and 24 include a diaphragm made of metal which will not interact with organic species or contribute impurities to the gas streams.

Conduits 26 and 28 carry the gases downstream from the pressure regulators 22 and 24 to high accuracy pressure sensors (or gauges) 30 and 32 which read the pressure of each gas in conduits 26 and 28 and display them to an operator/user. The pressures are adjusted, as necessary, in accordance with the gauge readings to achieve the desired flow rate. The conduits 26 and 28 then carry the pressure regulated gases to a "sonic blender" 38. This mixing apparatus 38, constructed in accordance with the present invention, is shown in FIG. 3.

The sonic blender 38 comprises two calibrated orifices 40 and 42 and a 'T'-shaped mixing chamber 44 which directs the final, diluted gas to the device to be calibrated (or to a storage vessel). The exact proportion of the diluted gas is determined by the size of the orifice, as well as the pressure and density of the gases.

The method and apparatus of the present invention relies on the use of "critical" flow through two calibrated orifices (e.g. 40 and 42 in FIG. 3). The velocity of gas through a sufficiently small orifice will eventually reach a maximum value as the differential pressure across the orifice increases. This maximum value is the so-called "critical" flow condition which occurs when the velocity of the gas through the orifice is equal to the local sonic velocity. In the case of nitrogen, the critical flow condition occurs when the upstream pressure is approximately twice the downstream pressure value.

In the present invention, gases are made to flow through the two calibrated orifices at sonic velocity (by regulating the upstream pressure) to insure accurate flow control. This system is used to achieve accurate proportional mixing of the two gases, which proportion is ultimately determined by the size of the orifices, the upstream pressure and the density of the gases.

FIG. 4 is a graph showing the linear relationship between flow and pressure for a typical calibrated orifice (0.002 inches in diameter in the present case). This linear relationship is described by the following equation:

$$\text{Flow} = 1.4755\,(P) + 14.942 \quad (1)$$

where P = upstream pressure in psig $$\text{Flow} = 1.4755\,(P) - 6.75 \quad (2)$$

where P = upstream pressure in psia

In order to approximate this pressure/flow relationship without conducting any measurements, a well known formula may be used (see, e.g. "Fluid Dynamics," J. W. Daily and R. F. Harleman, Addison, Wesley, Ready, 1966).

If $F$ = Flow in sccm $$F = 7.6 \times 10^8 (A)(P) \quad (3)$$

where
$A$ = area of orifice in m² and
$P$ = upstream pressure in psia
Substituting $A = \pi\,(0.001\text{ in})^2 = 2.03 \times 10^{-9}$ m² yields $$F = 1.55(P) \quad (4)$$

As can be seen by comparing the theoretical formula (equation 4) and the formula derived from the direct measurement of the flow (equation 2), a substantial increase in accuracy is achieved by direct measurement versus the theoretic calculated value based on the orifice diameter. The discrepancy between the measured slope (the measured flow value) and the calculated (theoretical) flow value may be attributed to non-ideal orifice shape which causes a difference between its effective and actual size. It may also be due to inaccuracies in orifice size measurement. Similarly, relying on measured results yield a non-zero intercept ($F = -6.75$ sccm at $P = 0$ psia). This is because critical flow does not occur at low pressure (i.e. until the pressure ratio on the opposite sides of the orifice reaches 2:1).

The concentration of a resultant mixture ($C_R$) prepared in accordance with the present system and method can be calculated as follows:

$$C_R = \frac{F_S C_S + F_D C_D}{F_S + F_D} \quad (5)$$

where F represents gas flow, C represents impurity (organic compound) concentration, the subscript S refers to the standard gas and the subscript D refers to the dilution gas.

If $C_D=0$, i.e. if the dilution gas is completely free of the impurity of interest then:

$$C_R = \frac{F_S C_S}{F_S + F_D} \quad (6)$$

The pressure to flow relationship, as defined, can be used to effect a dilution. If a first pressure is selected and achieved for one gas source, the required flow and pressure can be selected for the second gas source to achieve a particular desired concentration. In using a first embodiment of the present invention, as shown in FIG. 2, an operator relies on pressure gauges 30 and 32 associated with the respective gas sources to adjust the gas flow through sonic blender 38 to match the calculated requirements to get the needed concentration.

A test was conducted comparing the FIG. 2 embodiment of the present invention with a high precision mass flow controller based system ("MFC"), as shown in FIG. 1. The analyzer was a gas chromatograph equipped with a flame ionization detector and a pre-concentrator. The results are shown in FIG. 5 as area versus concentration in parts per billion as generated by both systems. The slope of the line in FIG. 5 is calculated by reading the flows, from the MFCs' digital readouts, which correspond to measured dilutions. Then, the present invention was set to generate flows along the calculated line, and the measured dilutions were plotted. The close agreement between the results obtained through use of the present invention and the results obtained through the MFC reflects the relative accuracy of the present invention. A check of the results obtained against the results calculated through equation 6 verifies the ability to predict the final concentration of the standard based on the pressure/flow relationships.

In the embodiment of FIG. 2, it is possible that errors may be introduced by the pressure readings taken with the pressure sensors 30 and 32 since most, if not all, pressure sensors have some error in their readings. In other words, the use of two pressure measuring devices can result in multiple pressure reading errors. Such errors ultimately effect the accuracy of the dilution.

One way to address this error problem is to use high accuracy pressure sensing devices. Another way to minimize such errors is to rely on a single differential pressure gauge.

A second embodiment of the present invention, shown in FIG. 6, employs this second solution. Instead of a plurality of pressure sensors, this embodiment relies on a differential pressure gauge 46 which is connected to conduits 48 and 50 on either side of the sonic blender 38' and an absolute pressure gauge 52 on the dilution or standard gas side (this gauge may be connected to either gas side without impairing the operation of this embodiment).

If it is desired to prepare a particular low concentration standard, the pressure of the dilution gas is first set to the chosen value for the standard side (as indicated on the absolute pressure gauge 52 connected to the dilution gas side). Then, the pressure on the standard side is adjusted until the differential gauge 46 reads zero. This sets the proper pressure on the standard side. Lastly, the desired pressure on the dilution gas side is set according to the absolute pressure gauge 52. (The differential gauge may read off-scale, but as long as its rated pressure is not exceeded, it will not be damaged). In this way, most of the errors associated with two different gauges as in the FIG. 2 embodiment, cancel each other out.

Thus error cancellation can be illustrated by assuming that the error is the absolute gauge is a constant fraction, x, of its reading. Then, the error in $C_R$ will be given by the following equation where P stands for gas pressure and A stands for orifice area:

$$\Delta C_R = \frac{(1+x) P_S A_S C_S}{(1+x)(P_S A_S + P_D A_D)} - \frac{P_S A_S C_S}{P_S A_S + P_D A_D} \quad (7)$$
$$= 0$$

In this case, the gauge error cancel exactly. In practice, the assumption of constant percentage error is probably slightly inaccurate. The effect of a non-zero intercept in the pressure-flow relationship which generally occurs in practice (see FIG. 4) is neglected. This error is small and decreases with flow rate. Regardless of these considerations, a considerable reduction in error over a two gauge system is realized.

By way of example, if the absolute pressure gauge 52 is connected to the standard gas side and a pressure of 80 pounds is desired on the dilution gas side with a pressure of 50 pounds on the standard gas side, the pressure of the standard gas first is adjusted until the absolute pressure gauge reads 80 pounds. Then, the pressure of the dilution gas is adjusted until the differential pressure gauge reads 0. This sets the dilution gas pressure to exactly 80 pounds. Lastly, the standard gas pressure is adjusted until the absolute pressure gauge read 50 pounds.

If the absolute pressure gauge is omitted, the system may still deliver a single concentration when the pressures upstream of both orifices are equal. Using a form of the previous flow-concentration relationship, and neglecting the non-zero intercept of the pressure-flow relationship (i.e. assuming $F \propto PA$):

$$C_R = \frac{P_S A_S C_S}{P_S A_S + P_D A_D} \quad (8)$$

If $P_S = P_D$, then $$C_R = \frac{A_S}{A_S + A_D} C_S, \text{ independent of pressure.} \quad (9)$$

In practice, the non-zero intercept of the pressure-flow relationship introduces a pressure dependence to the resultant concentration even when the pressure upstream of both orifices are equal. The extent of this pressure dependence will depend on the particular orifices used. In one particular test of a system built in accordance with the present invention, the dilution factor varied from 0.022 at 20 psia to 0.025 at 100 psia with equal pressures upstream. Thus, the omission of the absolute pressures gauge may reduce the accuracy of the system.

In reality, the above considerations are generally of little concern since a regulator, with an absolute pressure gauge is usually used upstream of the critical orifice.

A similar, single concentration approach, is taken in a third embodiment, shown in FIGS. 7 and 8. A specialized pressure regulating device 54, which is designed to regulate an equal pressure between the two gases, is employed. As shown in FIG. 8, the device 54 preferably comprises a pair of high pressure inlets 56 and 58 through which the two gases initially flow. A pair of chambers 60 and 62 having valves 64 and 66 therein, receive the gases from the inlets 56 and 58. The action of the valves 64 and 66 is governed by a set spring 72 which provides the appropriate balance to achieve the regulated equal pressure. When the gases are at the appropriate equal pressures (which may be set manually with the set spring 72), the valves 64 and 66 close, in response to the pressure of the gases on the diaphragms 74, to stop the flow of the gases into second chambers 68 and 70. Finally, the regulated pressure gas flows out of the device 54 through outlets 74 and 76 toward the sonic blender 38". This embodiment thus provides only a single dilution since the regulator does not posses the capacity to vary the relative upstream pressures to the orifices of the sonic blender.

FIG. 9 represents an improved device and method according to the invention, particularly suited for an excellent mixing of the dilution gas and the standard gas, while avoiding turbulent flow of said gases (their flows must remain laminar). This improved mixing is made possible by using an additional mixing chamber 14 wherein at least one of the gases and preferably both gases (or gas mixtures) follow a convoluted path, e.g. in a coiled tubing, in order to increase the distance travelled by an average gas molecule after the mixing point of the two gases (compared to the distance travelled by an average gas molecule without this convoluted path). Preferably, the convoluted path, e.g. the coiled tubing will be provided with means to deflect the flow of at least the standard gas from the wall towards the centerline of the path, e.g. the tubing such as a foil strip with bent cuts as represented on FIG. 9a. Those or other means will also preferably break up the flow stream of both the standard and/or diluent gases into multiple sub-streams.

In order to carry out this mixing in good conditions, it is preferred, according to the invention, to provide a convoluted path sufficiently open to avoid large pressure drops across it, while providing preferably a foil (metal, . . . ) which disrupts the gas flow path so that it is no longer parallel to the tubing walls. Preferably, this foil will contact the tubing walls at multiple points so that the boundary layer is disturbed. To be completely efficient, this convoluted path should have a sufficient length that the flow is disrupted in the three dimensions and/or that it splits the standard gas flow into sub-streams to increase the speed of the diffusion of the gases.

On FIG. 9a, is shown of foil strip (e.g. in copper, electropolished stainless steel, etc., having a surface treated in a way known by one skilled in the art to avoid the generation of impurities and/or particles) 154 which is cut to the inside diameter of the tubing being used for the additional mixing chamber 146. Cuts are made on this strip inward toward the centerline of the foil and the edges of the cuts are bent up (like 156, 160, . . . ) or down (158, 162, . . . ), e.g. alternately.

The foil strip 154 with its cuts is then inserted into a piece of tubing 148, 150, 152 (of adequate material, e.g. as for the foil strip) along the diameter, thus creating a convoluted path in the tube as disclosed above. The tubing 148, 150, 152 with the foil inside (as exemplified on FIG. 9b) is then coiled, the foil strip 154 being present at least on a part of the length of the coiled part 146 of the tubing 148, 150, 152, which represents the additional mixing chamber on FIG. 9c. The end of the tube 148 is then welded to the output end of the Tee 44 while the end of the tube 150 is connected to the analyzer. Preferably, the foil strip contacts the tubing wall not only along the diameter of introduction of said strip in said coil, but also with at least some of the bent cuts along the inside wall of the tubing.

The present invention provides an accurate, portable system for preparing low concentration gas phase calibration standards. This system is used in conjunction with a simple methodology which yields results comparable to other larger and more expensive systems.

While reference has been made to specific hardware and functional elements, these are only meant to illustrative and one or ordinary skill in the art may alter such hardware and functional elements without departing from the spirit and intent of the invention.

What is claimed is:

1. A gas dilution system comprising:
   first and second gas storage means, said first gas storage means containing a pressurized standard gas and said second gas storage means containing a pressurized dilution gas;
   first and second conduit means for conducting gas from said first and second gas storage means, respectively;
   at least one sensor means for measuring the pressure of gas in at least one of said first and second conduit means;
   first and second orifices communicating with said first and second conduit means, respectively, each orifice being calibrated to conduct pressurized gas therethrough at constant velocity to provide respective gas flows in a proportion determined by the sizes of said orifices; and
   mixing chamber for receiving and combining the gases flowing through said first and second orifices, said mixing chamber means comprising tubing means for defining a convoluted path for at least one of the gases.

2. A gas dilution system according to claim 1 wherein said tubing means comprises coiled tubing.

3. A gas dilution system according to claim 2 wherein said coiled tubing includes deflection means therein for deflecting the flow of said at least one gas from an inner wall of said tubing toward a centerline of the path of said at least one gas.

4. An apparatus according to claim 1 further comprising pressure differential gauge means communicating with said first and second conduit means for comparing the pressure of gas in said first conduit means to the pressure of gas in said second conduit means.

5. An apparatus according to claim 4 wherein said sensor means is disposed in only one of said first and second conduit means and is operable to indicate a desired pressure of the gas flowing in said one conduit means and said pressure differential gauge means is operable to indicate substantially zero differential pressure when the pressure of the gas flowing in the other conduit means is equal, to said desired pressure, whereupon said sensor means is operable to indicate a predetermined pressure of the gas flowing in said one conduit means.

6. A gas dilution system comprising:

first and second gas storage means, said first gas storage means containing a pressurized standard gas and said second gas storage means containing a pressurized dilution gas;

first and second conduit means for conducting gas from said first and second gas storage means, respectively;

at least one sensor means for measuring the pressure of gas in at least one of said first and second conduit means;

first and second orifices communicating with said first and second conduit means, respectively, each capable of conducting pressurized gas therethrough at constant velocity; and mixing chamber means for combining the gases flowing through said first and second orifices and including coiled tubing for defining a convoluted path for at least one of the gases having a foil strip included therein for deflecting the flow of said at least one gas from an inner wall of said tubing toward a centerline of the path of said at least one gas thereby to disrupt gas flow such that said gas flow is not parallel to said inner wall.

7. A gas dilution system according to claim 6 wherein said foil strip contacts said inner wall at multiple points.

8. A gas dilution system according to claim 7 wherein said foil strip includes cuts directed inwardly toward a centerline of the foil strip, said cuts having edges alternately bent upwardly and downwardly.

9. A gas dilution system according to claim 8 wherein the coiled tubing and cut foil strip therein define a convoluted path for the combined standard gas and dilution gas.

10. A gas dilution system comprising:

first and second gas storage means, said first gas storage means containing a pressurized standard gas mixture and said second gas storage means containing a pressurized dilution gas;

first and second conduit means for conducting gas from said first and second gas storage means, respectively;

pressure differential gauge means communicating with said first and second conduit means for comparing the pressure of gas in said first conduit means with the pressure of gas in said second conduit means;

first and second orifices communicating with said first and second conduit means, respectively, each orifice being of a size for conducting pressurized gas therethrough at a constant velocity to provide respective gas flows in a proportion determined by the sizes of said orifices; and mixing chamber means for receiving and combining the gases conducted through said first and second orifices, said mixing chamber means comprising tubing means for defining a convoluted path for at least one of the gases.

11. An apparatus according to claim 10, further comprising an absolute pressure gauge for measuring the pressure of gas in one of said conduit means.

12. An apparatus according to claim 11, wherein said absolute pressure gauge is in communication with said first conduit means.

13. An apparatus according to claim 11, in which said absolute pressure gauge is in communication with said second conduit means.

14. A gas dilution system according to claim 10 wherein said tubing means comprises coiled tubing.

15. A gas dilution system according to claim 14 wherein said coiled tubing includes deflection means therein for deflecting the flow of said at least one gas from an inner wall of said tubing toward a centerline of the path of said at least one gas.

16. A gas dilution system comprising:

first and second gas storage means, said first gas storage means containing a pressurized standard gas mixture and said second gas storage means containing a pressurized dilution gas; first and second conduit means for conducting gas from said first and second gas storage means, respectively;

pressure differential gauge means communicating with said first and second conduit means for comparing the pressure of gas in said first conduit means with the pressure of gas in said second conduit means; first and second orifices communicating with said first and second conduit means, respectively, for conducting pressurized gas therethrough at a constant velocity; and mixing chamber means for combining the gases conducted through said first and second orifices and including coiled tubing for defining a convoluted path for at least one of the gases having a foil strip included therein for deflecting the flow of said at least one gas from an inner wall of said tubing toward a centerline of the path of said at least one gas thereby to disrupt gas flow such that said gas flow is not parallel to said inner wall.

17. A gas dilution system according to claim 16 wherein said foil strip contacts said inner wall at multiple points.

18. A gas dilution system according to claim 17 wherein said foil strip includes cuts directed inwardly toward a centerline of the foil strip, said cuts having edges alternately bent upwardly and downwardly.

19. A gas dilution system according to claim 18 wherein the coiled tubing and cut foil strip therein define a convoluted path for the combined standard gas mixture and dilution gas.

* * * * *

UNITED STATES PATENT AND TRADEMARK OFFICE
CERTIFICATE OF CORRECTION

PATENT NO. : 5,261,452

DATED : November 16, 1993

INVENTOR(S) : James J.F. McAndrew et al.

It is certified that error appears in the above-identified patent and that said Letters Patent is hereby corrected as shown below:

Claim 1, line 18 (column 8, line 40), after "chamber" insert --means--.

Signed and Sealed this

Seventeenth Day of May, 1994

Attest:

BRUCE LEHMAN

*Attesting Officer*     *Commissioner of Patents and Trademarks*